United States Patent
Jugl et al.

(10) Patent No.: US 10,780,232 B2
(45) Date of Patent: Sep. 22, 2020

(54) SYSTEM FOR CAP REMOVAL

(71) Applicant: Sanofi-Aventis Deutschland GMBH, Frankfurt am Main (DE)

(72) Inventors: Michael Jugl, Frankfurt am Main (DE); Stefan Blancke, Frankfurt am Main (DE); Axel Teucher, Frankfurt am Main (DE); Claudia Biedermann, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 139 days.

(21) Appl. No.: 15/778,513

(22) PCT Filed: Nov. 21, 2016

(86) PCT No.: PCT/EP2016/078263
§ 371 (c)(1),
(2) Date: May 23, 2018

(87) PCT Pub. No.: WO2017/089274
PCT Pub. Date: Jun. 1, 2017

(65) Prior Publication Data
US 2018/0353702 A1   Dec. 13, 2018

(30) Foreign Application Priority Data
Nov. 27, 2015 (EP) .................................... 15196694

(51) Int. Cl.
*A61M 5/32* (2006.01)
(52) U.S. Cl.
CPC ........ *A61M 5/3204* (2013.01); *A61M 5/3202* (2013.01)
(58) Field of Classification Search
CPC .......................... A61M 5/3204; A61M 5/3202
See application file for complete search history.

(56) References Cited

U.S. PATENT DOCUMENTS

| 5,098,400 A | 3/1992 | Crouse et al. |
|---|---|---|
| 7,094,223 B2 | 8/2006 | Brunel |

(Continued)

FOREIGN PATENT DOCUMENTS

| WO | WO 02/11799 | 2/2002 |
|---|---|---|
| WO | WO 2013/058697 | 4/2013 |

OTHER PUBLICATIONS

PCT International Preliminary Report on Patentability in International Appln. No. PCT/EP2016/078263, dated May 29, 2018, 6 pages.

(Continued)

*Primary Examiner* — Amber R Stiles
(74) *Attorney, Agent, or Firm* — Fish & Richardson P.C.

(57) ABSTRACT

The present disclosure relates to a pen injecting device for delivering a liquid medicament comprising a pen body and a needle is received in a first end of the pen body. The pen injecting device further comprises an inner needle shield, removeably located over the needle to enclose the needle, and an outer needle shield, removeably located over the inner needle shield to enclose the inner needle shield. The pen injecting device also comprises a pen cap removeably attached to the first end of the pen body so as to enclose the outer needle shield. The pen cap comprises an arm depending from an inside surface of the cap and extending away from the first end of the pen body toward the inner and outer needle shields, the arm having a sharp end so that, as the cap is removed from the body, the sharp end of the arm grips the inner or outer needle shield to retain it in the cap and expose the needle.

15 Claims, 6 Drawing Sheets (56) References Cited

U.S. PATENT DOCUMENTS

2007/0100292 A1* 5/2007 Kirchhofer ......... A61M 5/2033
                                                        604/208
2008/0269692 A1* 10/2008 James ................. A61M 5/3202
                                                        604/198
2011/0319864 A1* 12/2011 Beller ................. A61M 5/2033
                                                        604/506

OTHER PUBLICATIONS

PCT International Search Report and Written Opinion in International Appln. No. PCT/EP2016/078263, dated Feb. 14, 2017, 8 pages.

* cited by examiner

SYSTEM FOR CAP REMOVAL

CROSS REFERENCE TO RELATED APPLICATIONS

This application is a U.S. national stage application under 35 USC § 371 of International Application No. PCT/EP2016/078263, filed on 21 Nov. 2016, which claims priority to European Application No. 15196694.2, filed on 27 Nov. 2015, the entire contents of which are incorporated herein by reference.

TECHNICAL FIELD

This disclosure relates to a pen injector drug delivery device.

BACKGROUND

Pen injectors have application where regular injections by persons without formal medical training occur. This is common among patients where self-treatment enables effective management of their disease.

In some circumstances, pen injectors are used by patients of impaired physical ability. For example, some patients with diabetes lose sensitivity in their fingers, which makes it harder for them to operate the pen injector. Further, conventional injector devices typically require the user to remove the cap and the needle shields separately to expose the needle in order to make the device ready for injection. It shall be appreciated that infirm patients such as the elderly or physically impaired may find removing the needle shields more difficult than removing the cap due to the small size of the needle shields making them difficult to handle.

SUMMARY

A pen injecting device for delivering a liquid medicament comprises a pen body, a needle received in a first end of the pen body, an inner needle shield removeably located over the needle to enclose the needle, an outer needle shield removeably located over the inner needle shield to enclose the inner needle shield and a pen cap removeably attached to the first end of the pen body so as to enclose the outer needle shield. The pen cap comprises an arm depending from an inside surface of the cap and extending away from the first end of the pen body toward the inner and outer needle shields. The arm has a sharp end so that, as the cap is removed from the body, the sharp end of the arm grips the inner or outer needle shield to retain it in the cap and expose the needle. Both the inner and the outer needle shields are removed simultaneously in the same operation as removing the cap, thereby making the device easier for infirm patients to use.

The at least one engaging element may comprise a rib extending from the internal surface of the cap into abutting engagement with the outer needle shield.

The arm may extend into engagement with the inner needle shield.

The cap may further comprise a rib extending from the internal surface of the cap into abutting engagement with the outer needle shield.

The cap may comprise two ribs disposed opposite each other so that, as the pen cap is removed from the body, the outer shield is retained in the cap by frictional engagement of the outer shield with the ribs.

Therefore, the outer shield is removed as the cap is removed.

The arm may be biased away from the inside surface of the cap so that, as the pen cap is removed, the sharp end of the arm moves into engagement with and grips the inner needle shield.

The cap may comprise a second arm, the arm and second arm being disposed opposite each other so that, as the pen cap is removed, the sharp ends of respective arms engage with the inner needle shield to pinch the shield so that the inner needle shield is retained in the cap.

Therefore the inner shield is also removed as the cap is removed so that both the inner and outer needle shields are removed simultaneously.

The arm may be configured to extend toward the outer needle shield, the sharp end of the arm abutting the outer needle shield so that, as the pen cap is removed, the sharp end of the arm pierces the outer needle shield, and having pierced the outer needle shield, engages with the inner needle shield so that both the inner and outer needle shields are retained in the cap.

Therefore, the arm engages both the inner and outer needle shields so that the inner and outer needle shields are removed simultaneously as the cap is removed.

The arm may be biased toward the outer needle shield.

Therefore, the sharp end of the arm grips the outer needle shield so that, as the cap is removed, the sharp end of the arm penetrates the outer needle shield to engage the inner needle shield.

The cap may comprise a second arm, the arm and second arm being disposed opposite each other so that, as the pen cap is removed, the sharp ends of the respective arms pierce the outer needle shield and engage with the inner needle shield to pinch the inner needle shield so that both the inner and outer needle shields are retained in the cap.

The outer needle shield may comprise a region of reduced wall thickness adjacent the sharp end of each arm.

Therefore, less force is required to penetrate the outer needle shield which reduces the force required to remove the cap. This benefits patients with reduced dexterity or reduced sensitivity in their fingers who may struggle to grip the cap to exert sufficient force to remove the cap.

A pen injecting device as described above comprises a cartridge of liquid medicament.

So that the present invention may be more fully understood embodiments thereof will now be described with reference to the accompanying drawings in which:

DETAILED DESCRIPTION OF THE FIGURES

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1A:
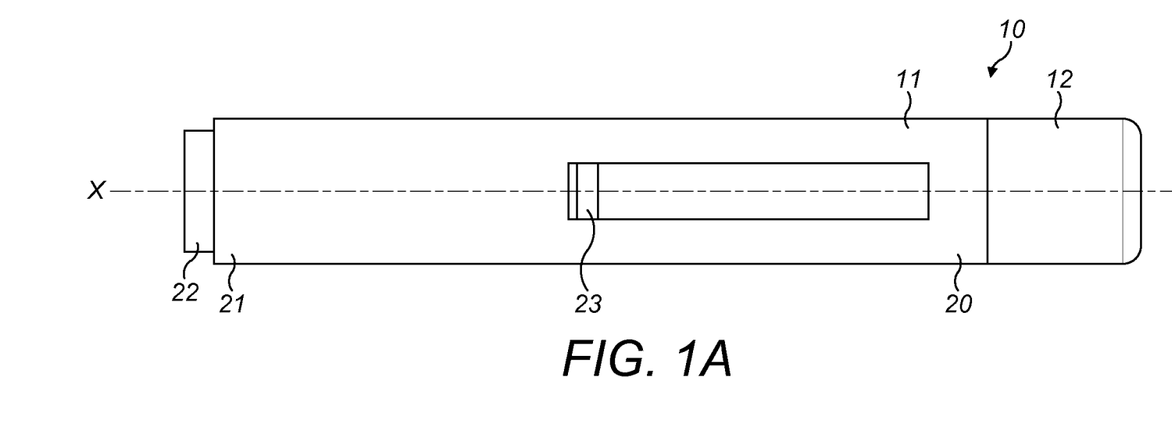
FIG. 1A shows a drug delivery device with a cap attached.
Figure 1B:
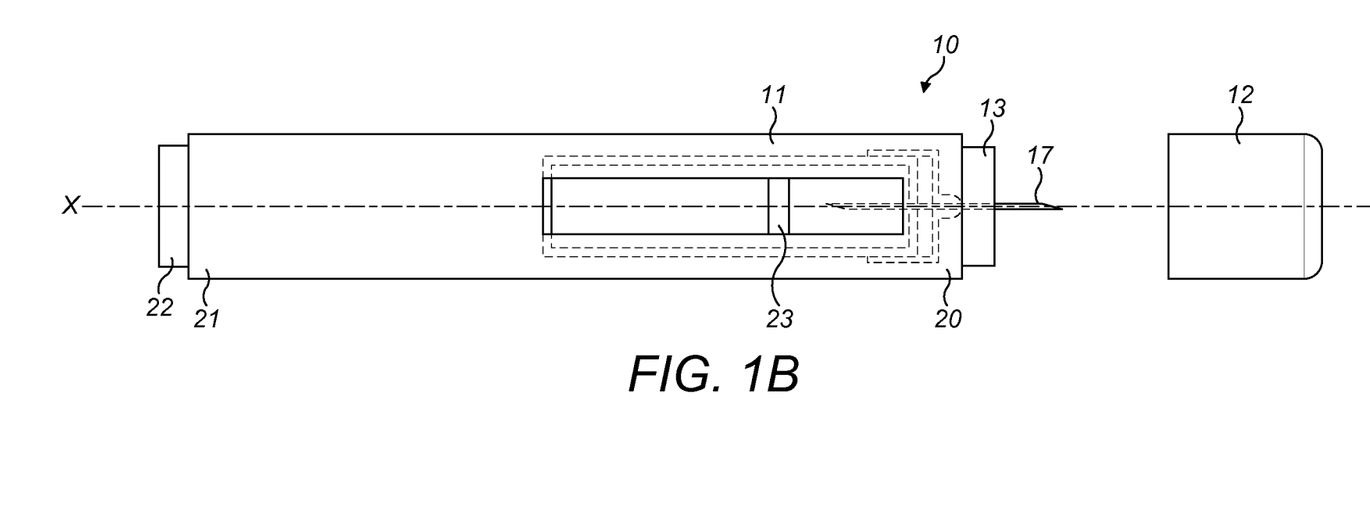
FIG. 1B shows a drug delivery device with the cap removed.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically, a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2:
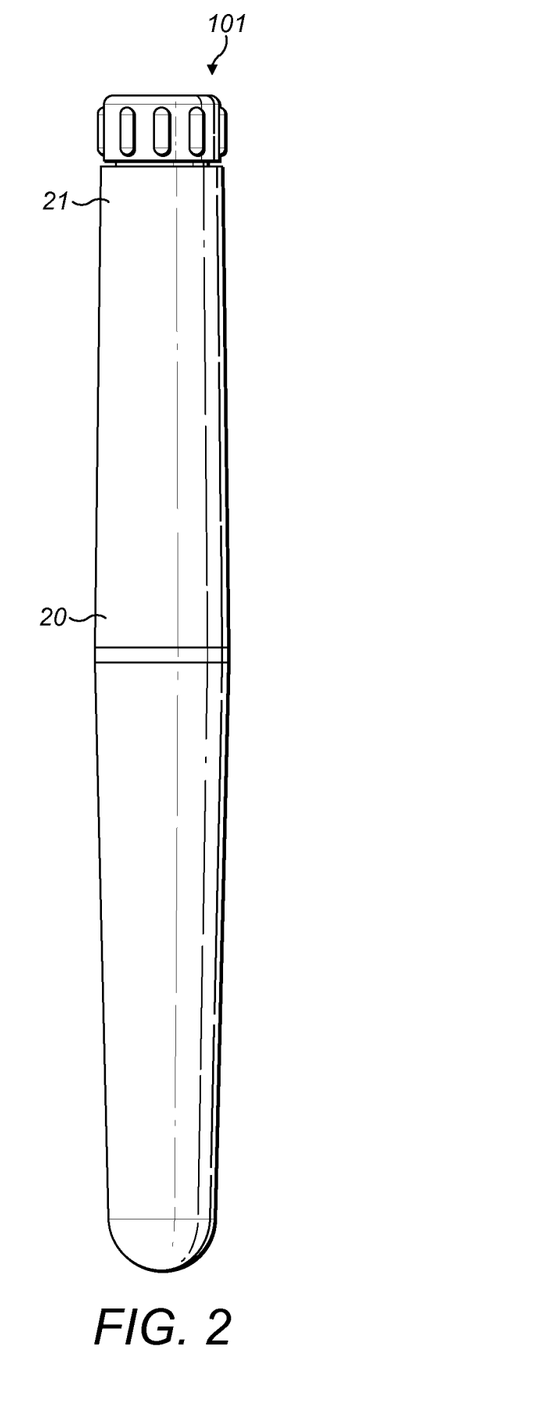
FIG. 2 shows a pen injector with a cap attached.

A typical pen injector 101 as shown in FIG. 2 is described in more detail herein for reference. The pen injector 101 has a proximal region 21 (upper end in FIG. 2) and a distal region 20 (lower end in FIG. 2).

Figure 3A:
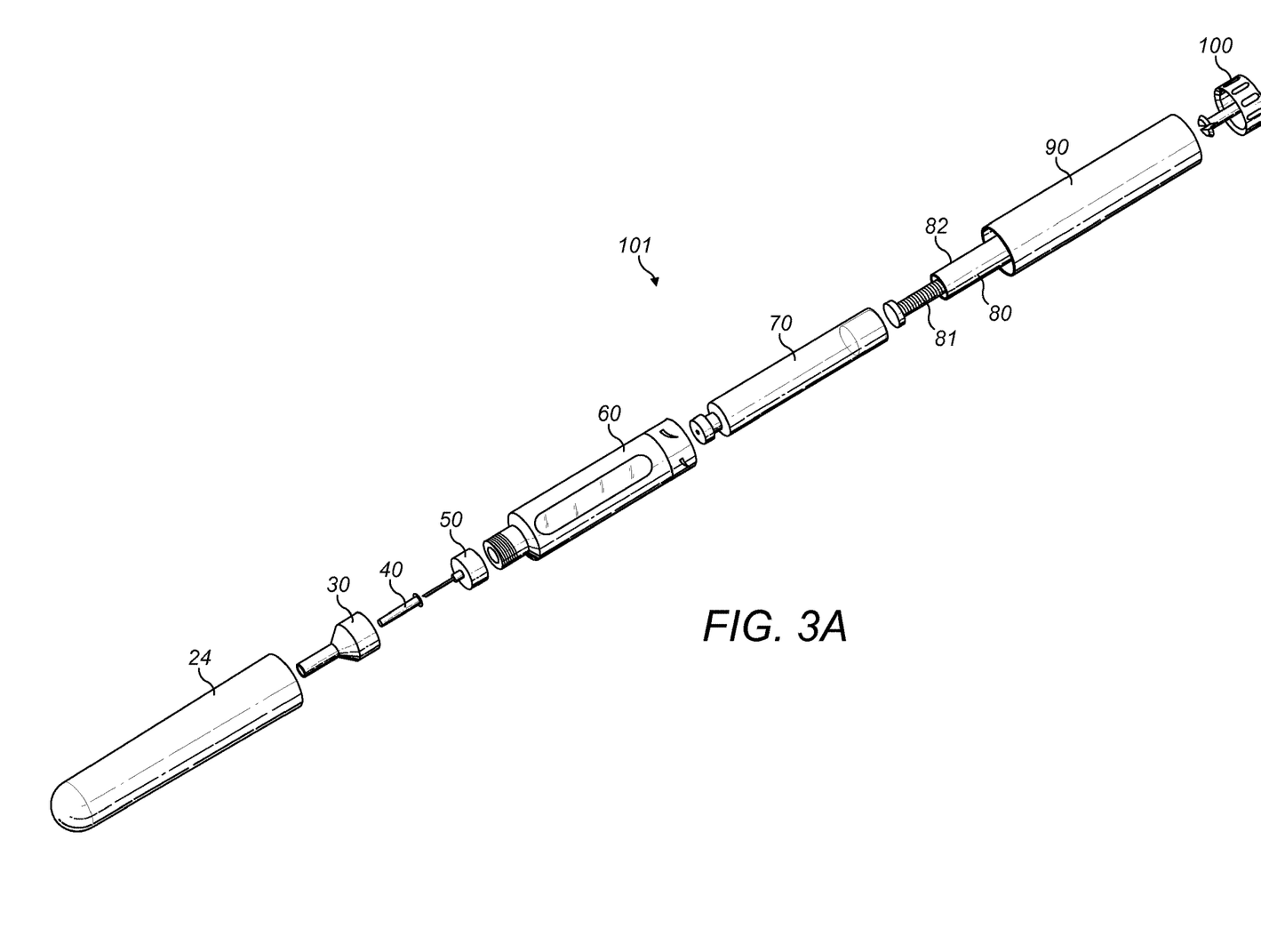
FIG. 3A shows an exploded view of the components of the pen injector shown in FIG. 1.

According to some embodiments of the present disclosure, the component parts of a manually operated pen injector 101 are shown in FIG. 3A in more detail. The pen injector 101 comprises an injector cap 24, an outer needle shield 30, an inner needle shield 40, a needle holder 50, a cartridge holder 60, a medicament cartridge 70, a plunger mechanism 80, an outer housing 90 and a dispense button 100.

Figure 3B:
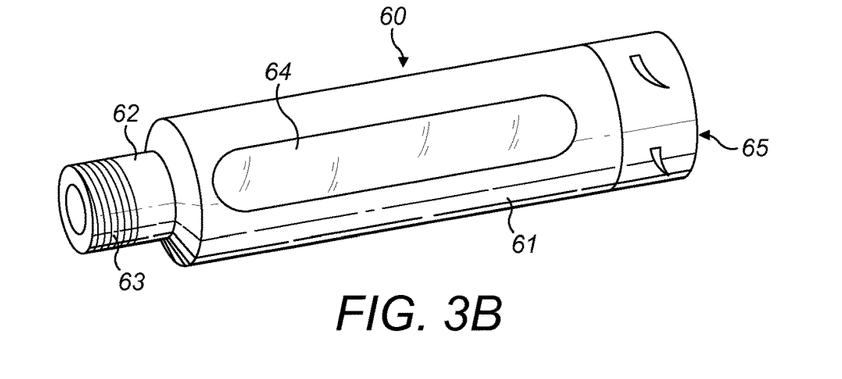
FIG. 3B shows a component of the pen injector shown in FIG. 1.

The cartridge holder 60, shown in FIG. 3B, is substantially tubular and has a constant diameter section 61 with an opening 65 formed in a proximal end of the cartridge holder 60 to receive the medicament cartridge 70. The cartridge holder 60 further comprises a section of reduced diameter 62 extending to a distal end on which an external thread 63 is provided. A portion of the constant diameter section 61 is provided with a transparent panel, herein a window 64, so that a user can see through the cartridge holder 60 to determine the quantity of medicament remaining in the cartridge 70.

Figure 3C:
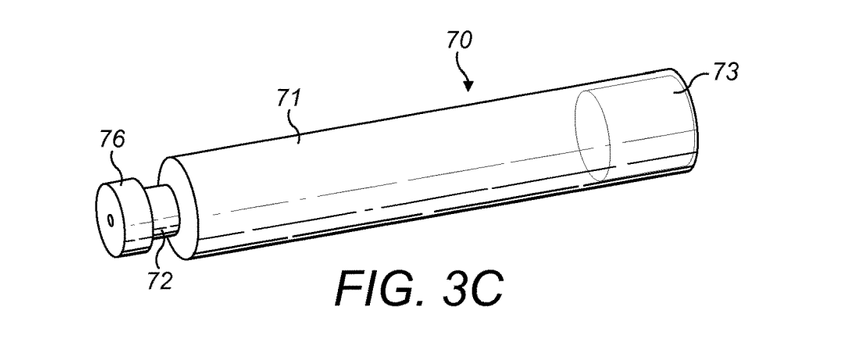
FIG. 3C shows a component of the pen injector shown in FIG. 1.

The medicament cartridge 70, shown in FIG. 3C, is a tubular container for storing liquid medicament. The cartridge 70 comprises a first diameter section 71 and a second diameter section 72, the first diameter section 71 is fitted securely within the constant diameter section 61 of the cartridge holder 60 so that an outer surface of the first diameter section 71 lightly abuts an inner surface of the constant diameter 61 of the cartridge holder 60. The first diameter section 71 has an open proximal end in which a cylindrical rubber stopper 73 is received. The cylindrical rubber stopper 73 has an outer surface that tightly abuts with an inside surface of the first diameter section 71 to seal the proximal end of the cartridge 70. The second diameter section 72 extends to a distal end of the cartridge 70 and has a smaller diameter than the first diameter section 71 so that the second diameter section 72 of the cartridge 70 fits within the reduced diameter section 62 of the cartridge holder 60.

Figure 3D:
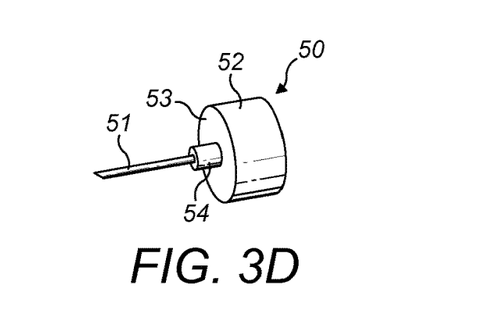
FIG. 3D shows a component of the pen injector shown in FIG. 1.
Figure 3E:
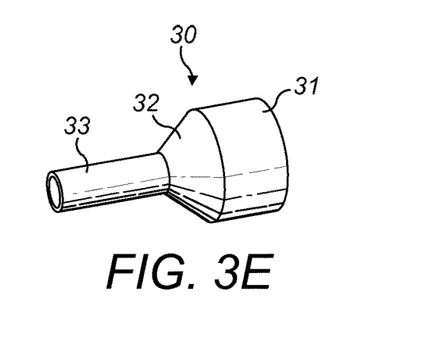
FIG. 3E shows a component of the pen injector shown in FIG. 1.

FIGS. 3D and 3E show the needle holder 50 and the outer needle shield 30 respectively, both will be described in more detail below.

Figure 4:
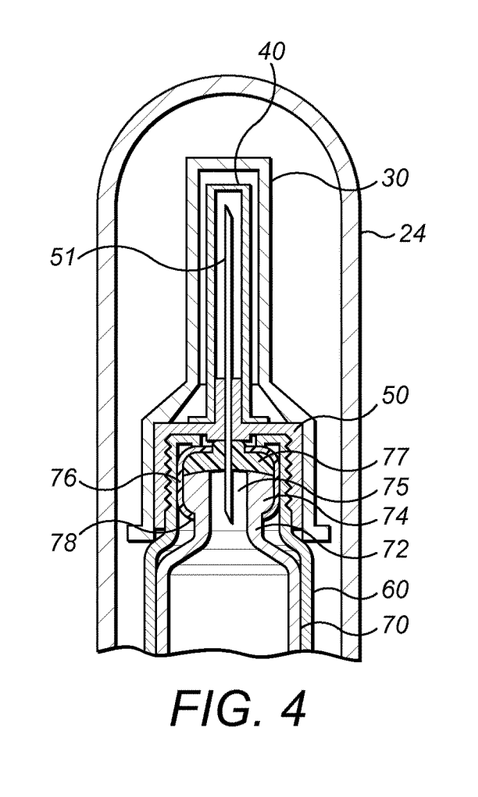
FIG. 4 is a partial section view of the pen injector shown in FIG. 1.

Referring now to FIG. 4, a partial section view of an assembled injector pen 101 is shown. It can be seen that the second diameter section 72 of the medicament cartridge 70 further comprises a lip 74 that extends outwardly beyond the second diameter section 72 and around the full circumference of the second diameter section 72. The lip 74 is disposed adjacent an opening 75 in the distal end of the cartridge 70 and provides an edge over which a rubber cap 76 is located to seal the cartridge 70.

The rubber cap 76 has a disc portion 77 that abuts the distal end of the cartridge 70 and locates over the opening 75 to seal the cartridge 70. A needle 51 is received through the disc portion 77 to communicate with the inside of the cartridge 70 and provide a conduit along which the liquid medicament can travel during dispense, when the medicament is delivered to a subcutaneous region of the patient. A cylindrical wall 78 of the rubber cap 76 extends around the outer edge of the disc portion 77 and is located over the lip 74 of the cartridge 70 to hold the rubber cap 76 in tightly abutting relation with the cartridge 70.

As can be seen from FIG. 4, an outer surface of the cylindrical wall 78 of the rubber cap 76 locates against an inner surface of the section of reduced diameter 62 of the cartridge holder 60. The respective surfaces are tightly abutted so that the cartridge 70 is securely held within the cartridge holder 60. It can also be seen that the needle 51 is received through the disc portion 77 of the rubber cap 76 and through the opening 75 provided in the distal end of the cartridge 70 to communicate with the inside of the cartridge 70.

The needle 51 is secured in place by the needle holder 50, shown in FIG. 3D, which locates against the reduced diameter section 62 of the cartridge holder 60 as shall be described herein. The needle holder 50 comprises a tubular threaded portion 52 having a cylindrical wall with an internal thread. The threaded portion 52 is configured to locate over the reduced diameter section 62 of the cartridge holder 60 by threaded engagement with the external thread 63 of the cartridge holder 60. A needle supporting portion 53 of the needle holder 50 encloses a distal end of the cylindrical wall and supports the needle 51 in an axial position relative to the cylindrical wall. The needle 51 extends through the needle supporting portion 53 and into the cartridge 70 as shown in FIG. 4.

A shoulder 54 is provided on the needle supporting portion 53 for an inner needle shield 40 to locate against when the device is not in use. The shoulder 54 extends around the needle 51 where the needle 51 meets the needle supporting portion 53 to provide a cylindrical protrusion over which the inner needle shield 40 locates.

The inner needle shield 40 is tubular with an open proximal end and a blind distal end. The diameter of the inner needle shield 40 is such that an internal surface of the needle shield 40 tightly abuts the shoulder 54 of the needle holder 50 to securely locate the needle shield 40 thereon. With the inner needle shield 40 thus located, the needle 51 is fully enclosed.

The outer needle shield 30, shown in FIG. 3E, is disposed over the inner needle shield 40 to locate against the needle holder 50. The outer needle shield 30 is tubular having an open proximal end and a blind distal end. The outer needle shield 30 comprises a proximal section 31 having a first diameter that extends between the proximal end and a connecting section 32. The connecting section 32 converges toward a proximal section 33, which extends to the distal end. The distal section 33 has a second diameter, which is smaller than the first diameter. The proximal section 31 locates over an outer surface of the cylindrical wall of the needle holder 50 with the diameter of the proximal section 31 being such that an internal surface of the proximal section 31 tightly abuts the outer surface of the needle holder tubular portion 52 to securely locate the outer needle shield 30 thereon. The diameter of the distal section 33 is such that an internal surface of the distal section 33 lightly abuts an outer surface of the inner shield 40.

The outer housing 90 is tubular with open distal and proximal ends. The proximal end of the cartridge holder 60 is received in the distal end of the outer housing 90 and is retained therein by threaded engagement. The plunger mechanism 80 is slideably disposed in the outer housing 90 and is configured to exert axial load upon the rubber stopper 73 to displace the rubber stopper 73 down the cartridge 70 during dispense. A button 100 is provided to operate the plunger mechanism 80 and is disposed protruding from the proximal opening of the housing 90. The button 100 allows the user of the device to set the required dose of liquid medicament to be delivered during dispense. In common examples of such devices, the dose is set by twisting the button 100 so that it rotates around the housing 90 axis. In such examples, the plunger mechanism 80 comprises a threaded bar 81 that extends through the outer housing and a plunger sleeve 82 which is disposed within the housing 90 and partially extends over the threaded bar 81. The plunger sleeve 82 is tubular with an internal thread which is in threaded engagement with the threaded bar 81 along a distal portion of its length. A proximal portion of the plunger sleeve 82 extends to the proximal opening of the housing 90 where it is mechanically coupled to the button 100. Therefore rotation of the button 100 causes the sleeve 82 to react against the threaded bar 81 so that it is displaced along the threaded bar 81, the button 100 being rotatable in a direction to cause proximal portion of the sleeve 82 to be extended from the proximal opening of the housing 90. A clicker provides acoustic and haptic feedback as the button 100 is rotated to indicate the dose selected for dispense. Once the dose has been selected, dispense can be effected by applying an axial load to the button 100 to displace the button 100 back toward the proximal opening of the housing 90. The axial load is transferred from the button 100 to the threaded bar 81 via the sleeve 82, and from the threaded bar 81 to the rubber stopper 73 received in the cartridge 70.

The injector cap 24 is removeably attached to the distal end of the outer housing 90. The cap 24 is tubular having an open proximal end and a blind distal end. The distal end of the outer housing is received in the open proximal end of the pen cap so that an internal surface of the cap 24 abuts an external face of the outer housing 90. The cap 24 encloses the cartridge holder 60, the needle 51 and the associated needle shields 40, 30.

Figure 5A:
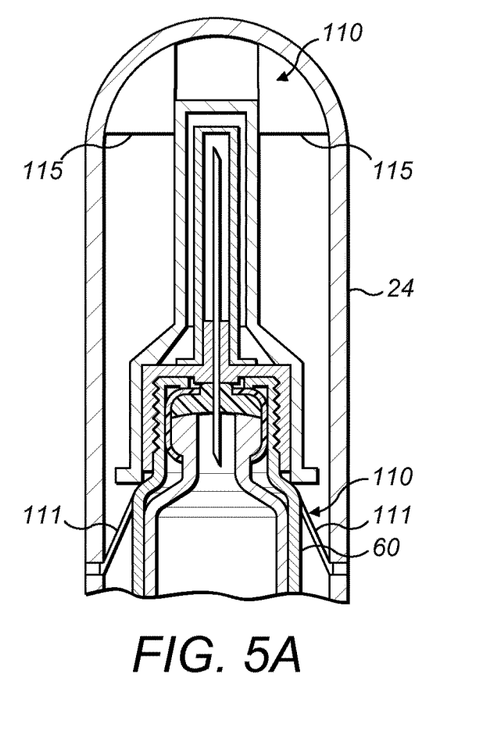
FIG. 5A is a partial section view of a pen injector with a cap attached according to a first embodiment.
Figure 5B:
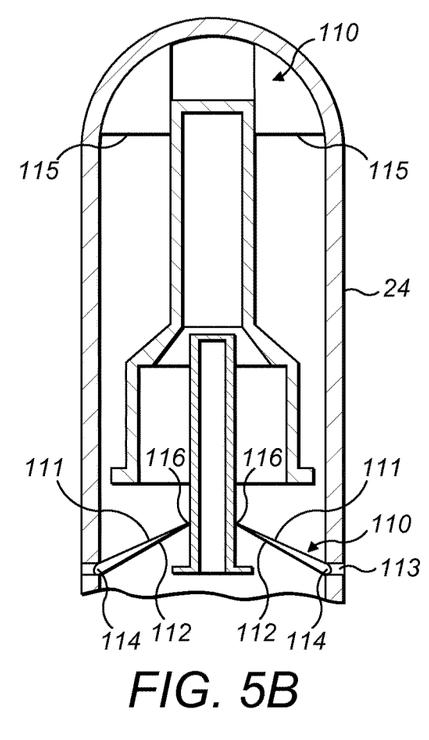
FIG. 5B is a partial section view of the pen injector of FIG. 4A with the cap removed.
Figure 6A:
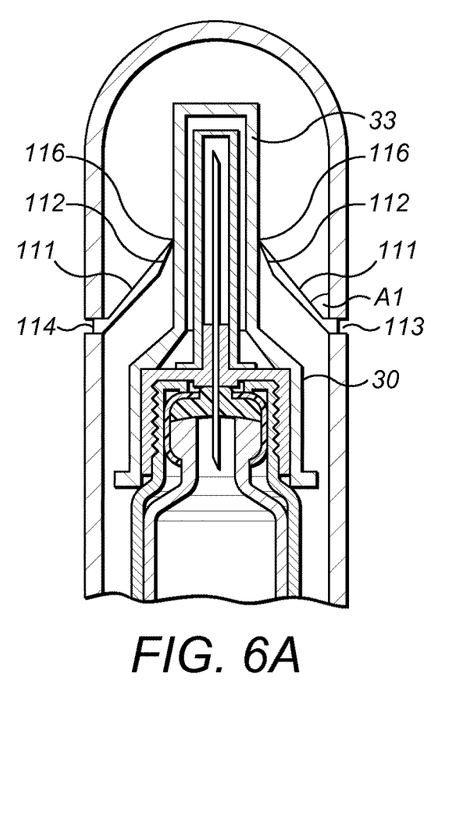
FIG. 6A is a partial section view of a pen injector with a cap attached according to a second embodiment.
Figure 6B:
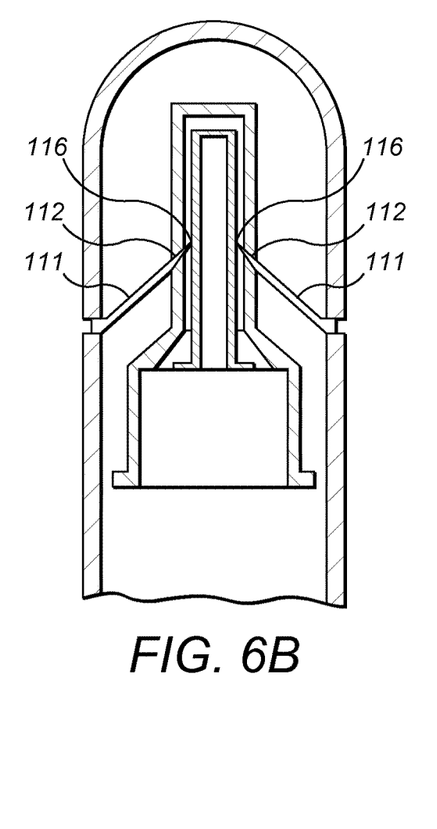
FIG. 6B is a partial section view of the pen injector of FIG. 5A with the cap removed.
Figure 7:
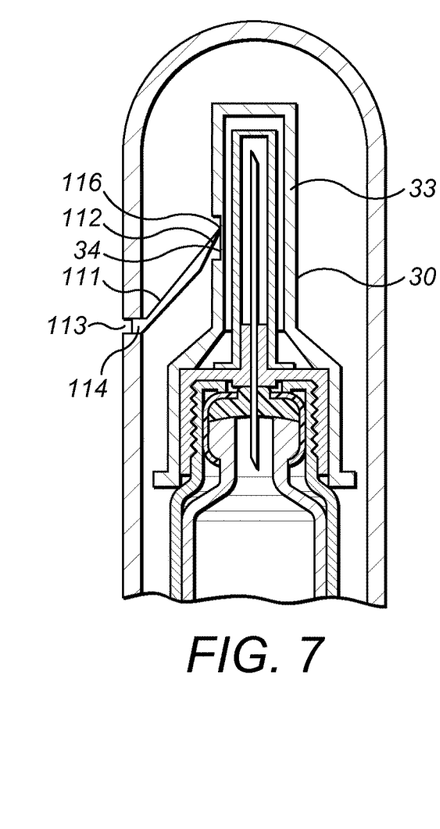
FIG. 7 is a partial section view of a pen injector with a cap attached according to a third embodiment.

According to embodiments shown in FIGS. 5 to 7, the pen cap further comprises engagement elements 110 to engage with the inner needle shield 40 and the outer needle shield 30 as the cap 24 is removed from the outer housing 90 so that, when the cap is removed from the outer housing 90, the inner and outer needle shields 40/30 are retained in the cap 24 to expose the needle 51.

According to a first embodiment shown in FIGS. 5A and 5B, the engagement elements 110 comprise two arms 111 to engage with the inner needle shield 40 as the cap 24 is removed. The arms 111 are disposed between the cap 24 and the cartridge holder 60. Each arm 111 is an elongate needle-like protrusion that extends obliquely away from the inner surface of the cap 24 toward the distal end of the cap 24 and comprises a tapered section 112, which thins to a sharply pointed tip 116. The arms 111 are secured to the internal surface of the pen cap by a recessed pocket 113 into which a base section 114 of the arm extends.

The engagement elements further comprise at least two ribs 115 that extend from the internal surface of the cap 24 adjacent the distal end of the cap 24. Each rib 115 extends radially from the internal surface of the cap 24 into tightly abutting relation with the outer needle shield 30. The ribs 115 are disposed opposite each other so that the outer needle shield 30 is tightly gripped by the ribs 115. Therefore, the outer needle shield 30 is retained in the cap 24 as the cap 24 is removed from the housing 90.

In one example of this embodiment, the arms 111 may be sprung such that the tips of the arms 111 are biased away from the inner surface of the cap 24. In such examples of this embodiment, the arms 111 are securely located in the recessed pocket 113 and are cantilevered inwards so that the tapered portion 112 of the arms 111 abuts the cartridge holder 60. Therefore, as the cap 24 and the outer needle shield 30 are removed, the tapered portion 112 passes over the tubular portion 52 of the needle holder 50 to bend toward the inner needle shield 40. The pointed tips 116 of the arms 111 contact the inner needle shield 40 so that the arms 111 grip the inner needle shield 40. The arms 111 are disposed opposite each other such that removal of the cap 24 causes the inner needle shield 40 to be pinched between opposing pointed tips 116 of the respective arms 111. Therefore, the inner needle shield 40 is retained in the cap 24 as the cap 24 is removed from the injector housing 90.

With the cap 24 removed from the housing 90 according to the first embodiment, the inner and outer needle shields 40/30 are retained in the cap 24 as shown in FIG. 5B.

Although in FIGS. 5A and 5B only two arms 111 are shown, it shall be appreciated that in other examples of this embodiment more than two arms 111 are provided. In one such example, two pairs of arms 111 are provided with each arm 111 of each pair disposed opposite each other such that removal of the cap 24 causes the inner needle shield 40 to be pinched between opposing pointed tips 116 of the respective pairs of arms 111.

In a second embodiment shown in FIGS. 6A and 6B, the arms 111 are configured to engage both the inner and outer needle shields 40/30 as the cap 24 is removed. As in the first embodiment, each arm 111 extends obliquely away from the inner surface of the cap 24 toward the distal end of the cap 24 and comprises a tapered portion 112, which thins to a sharply pointed tip 116. The arms 111 are secured to the internal surface of the cap 24 by a recessed pocket 113 into which a base section 114 of the arm 111 extends. In this embodiment, the arms 111 are disposed between the cap 24 and the distal section 33 of the outer needle shield 30 so that the pointed tips 116 of the arms abut the distal section 33 of the outer needle shield 30 to grip the outer needle shield 30. The arms 111 are disposed opposite each other such that removal of the cap 24 causes the outer needle shield 30 to be pinched between opposing pointed tips 116 of the respective arms 111. As the cap 24 is removed, the tips 116 of the arms 111 penetrate the outer needle shield 30 to extend through the outer needle shield 30 and grip the inner needle shield 40. Therefore, the inner and outer needle shields 30/40 are retained in the cap 24 as the cap 24 is removed from the housing 90.

It shall be appreciated that the angle A1 at which the arms 111 are disposed relative to the outer needle shield 30 is configured to ensure a sufficient component of the axial force used to remove the cap 24 is transferred by the arms 111 into the outer needle shield 30 to cause penetration of the outer needle shield 30. If the angle A1 is too small, insufficient force will be transferred through the arms 111 for penetration of the outer needle shield 30 to occur.

With the cap 24 removed from the housing 90 according to the second embodiment, the inner and outer needle shields 40/30 are retained in the cap 24 as shown in FIG. 6B.

Although in FIGS. 6A and 6B only two arms 111 are shown, it shall be appreciated that in other examples of this embodiment more than two arms 111 are provided. In one such example, two pairs of arms 111 are provided with each arm 111 of each pair disposed opposite each other such that removal of the cap 24 causes the outer needle shield 30 to be pinched between opposing pointed tips 116 of the respective pairs of arms 111.

According to a third embodiment shown in FIG. 7, the distal portion 33 of the outer needle shield 30 comprises a region of reduced wall thickness 34. In this embodiment a single arm 111 is provided, wherein the arm 111 extends obliquely away from the internal surface of the cap 24 toward the distal end of the cap 24 and comprises a tapered portion 112, which thins to a sharply pointed tip 116. The arm 111 is secured to the internal surface of the cap 24 by a recessed pocket 113 into which a base section 114 of the arm 111 extends. The arm 111 is disposed between the cap 24 and the distal section 33 of the outer needle shield 30 with the pointed tip 116 of the arm 111 abutting the region of reduced wall thickness 34. As the cap 24 is removed, the tip 116 of the arm 111 penetrates the region of reduced wall thickness 116 of the outer needle shield 30 to extend through the outer needle shield 30 and grip the inner needle shield 40. Therefore, the outer and inner needle shields 30/40 are retained in the cap 24 as the cap 24 is removed from the housing 90.

It shall be appreciated that substantially less force is required to cause the arm 111 of the third embodiment to penetrate the region of reduced wall thickness 34 of the outer needle shield 30 than is required to penetrate the outer needle shield 30 of the first and second embodiments. Therefore, advantageously, less axial force is required to remove the cap 24 of the third embodiment than is required to remove the cap 24 of the first or second embodiments.

It shall be appreciated that the embodiment shown in FIG. 7 is not limited to a single arm 111. In further examples of this embodiment, more than one arm 111 is provided with the pointed tip 116 of each arm 111 abutting a respective region of reduced wall thickness 34.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15$^{th}$ edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten. An example of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor-binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof

The invention claimed is:

1. A pen injecting device for delivering a liquid medicament comprising:
   a pen body,
   a needle received in a first end of the pen body,
   an inner needle shield removeably located over the needle to enclose the needle,
   an outer needle shield removeably located over the inner needle shield to enclose the inner needle shield, and
   a pen cap removeably attached to the first end of the pen body so as to enclose the outer needle shield, wherein the pen cap comprises an arm depending from an inside surface of the pen cap and extending away from the first end of the pen body toward the inner and the outer needle shields, the arm having a sharp end so that, as the pen cap is removed from the pen body, the sharp end of the arm is moved relative to and into engagement with the inner needle shield to grip the inner needle shield to retain the inner needle shield in the pen cap and expose the needle.

2. The pen injecting device according to claim 1, wherein the arm extends into engagement with the inner needle shield, and wherein the pen cap further comprises a rib extending from an internal surface of the pen cap into abutting engagement with the outer needle shield.

3. The pen injecting device according to claim 2, wherein the pen cap comprises two ribs disposed opposite each other so that, as the pen cap is removed from the pen body, the outer needle shield is retained in the pen cap by frictional engagement of the outer needle shield with the ribs.

4. The pen injecting device according to claim 3, wherein the arm is biased away from the inside surface of the pen cap so that, as the pen cap is removed, the sharp end of the arm moves into engagement with and grips the inner needle shield.

5. The pen injecting device according to claim 4, wherein the pen cap comprises a second arm, the arm and the second arm being disposed opposite each other so that, as the pen cap is removed, the sharp ends of the respective arms engage with the inner needle shield to pinch the inner needle shield so that the inner needle shield is retained in the pen cap.

6. The pen injecting device according to claim 1, wherein the arm is configured to extend toward the outer needle shield, the sharp end of the arm abutting the outer needle shield so that, as the pen cap is removed, the sharp end of the arm pierces the outer needle shield, and having pierced the outer needle shield, engages with the inner needle shield so that both the inner and outer needle shields are retained in the pen cap.

7. The pen injecting device according to claim 6, wherein the arm is biased toward the outer needle shield.

8. The pen injecting device according to claim 1, wherein the pen cap comprises a second arm, the arm and second arm being disposed opposite each other so that, as the pen cap is removed, the sharp ends of the respective arms pierce the outer needle shield and engage with the inner needle shield to pinch the inner needle shield so that both the inner and outer needle shields are retained in the pen cap.

9. The pen injecting device according to claim 1, wherein the outer needle shield comprises a region of reduced wall thickness adjacent the sharp end of the arm.

10. The pen injecting device according to claim 9, wherein the outer needle shield comprises a second region of reduced wall thickness adjacent a sharp end of a second arm, wherein the second arm is disposed opposite the arm in the pen cap.

11. The pen injecting device according to claim 1, further comprising a cartridge containing the liquid medicament.

12. The pen injecting device according to claim 1, wherein the inner needle shield is movable relative to the outer needle shield.

13. A method comprising:
   gripping a first needle shield disposed on a drug delivery device with a sharp end of at least one arm that extends from a pen cap to retain the first needle shield in the pen cap, wherein the sharp end of the at least one arm is moved relative to and into engagement with the first needle shield when the pen cap is removed, wherein the pen cap is releasably engaged with the drug delivery device; and
   gripping a second needle shield disposed on the drug delivery device to retain the second needle shield in the pen cap, and
   wherein the first needle shield is an inner needle shield and the second needle shield is an outer needle shield and the outer needle shield is removeably located over the inner needle shield.

14. The method according to claim 13, wherein gripping the first needle shield comprises engaging a section of the first needle shield with the sharp end of the arm, such that the first needle shield and the pen cap are translationally coupled.

15. The method of claim 13, wherein gripping the second needle shield comprises engaging a section of the second needle shield with a rib extending from the pen cap such that the second needle shield and the pen cap are translationally coupled.

* * * * *